United States Patent
Baker, Jr.

(10) Patent No.: US 12,076,558 B2
(45) Date of Patent: Sep. 3, 2024

(54) METHODS, SYSTEMS, APPARATUSES, AND DEVICES FOR FACILITATING STIMULATING OF MUSCLES OF USERS

(71) Applicant: Gary Thomas Baker, Jr., Houston, TX (US)

(72) Inventor: Gary Thomas Baker, Jr., Houston, TX (US)

(*) Notice: Subject to any disclaimer, the term of this patent is extended or adjusted under 35 U.S.C. 154(b) by 393 days.

(21) Appl. No.: 17/482,214

(22) Filed: Sep. 22, 2021

(65) Prior Publication Data
US 2022/0088378 A1    Mar. 24, 2022

Related U.S. Application Data

(60) Provisional application No. 63/081,838, filed on Sep. 22, 2020.

(51) Int. Cl.
*A61N 1/36* (2006.01)
*A61N 1/18* (2006.01)
*G06F 3/01* (2006.01)

(52) U.S. Cl.
CPC ..... *A61N 1/36003* (2013.01); *A61N 1/36031* (2017.08)

(58) Field of Classification Search
CPC .... A61B 2562/0219; A61B 2562/0247; A61B 5/0803; A61B 5/296; A61F 2005/0155; A61F 2005/0174; A61F 2005/0188; A61F 5/0102; A61F 5/0125; A61F 5/0127; A61F 5/013; A61H 1/024; A61H 1/0266; A61H 1/0277; A61H 1/0285; A61H 2201/1215; A61H 2201/1635; A61H 2201/164; A61H 2201/165; A61H 2201/1676; A61H 2201/1697; A61H 2201/5007; A61H 2230/105; A61H 2230/605; A61N 1/36003; A61N 1/37288; A61N 1/3787

See application file for complete search history.

(56) References Cited

U.S. PATENT DOCUMENTS

2007/0208392 A1* 9/2007 Kuschner ........... A61N 1/37288 607/48
2018/0020951 A1* 1/2018 Kaifosh ................ A61B 5/389 607/48

* cited by examiner

*Primary Examiner* — Jon Eric C Morales

(57) ABSTRACT

A method and system for facilitating stimulating of muscles of users are provided. Further, the method may include a step of receiving muscle data from sensors, analyzing the muscle data, generating first muscle activity data of the muscles of first users based on the analyzing of the muscle data, receiving first biological metrics of the first users from first devices, receiving second biological metrics of second users from second devices, analyzing the first muscle activity data, the first biological metrics, and the second biological metrics, transforming the first muscle activities into second muscle activities of the muscles of the second users, generating muscle activation commands for the muscle activation of the muscles of the second users, transmitting the muscle activation commands to muscle stimulators disposable on body parts of the second users, and storing the first muscle activity data and the muscle activation commands.

18 Claims, 10 Drawing Sheets

METHODS, SYSTEMS, APPARATUSES, AND DEVICES FOR FACILITATING STIMULATING OF MUSCLES OF USERS

The current application claims a priority to the U.S. Provisional Patent application Ser. No. 63/081,838 filed on Sep. 22, 2020.

TECHNICAL FIELD

Generally, the present disclosure relates to the field of data processing. More specifically, the present disclosure relates to methods, systems, apparatuses, and devices for facilitating stimulating of muscles of users.

BACKGROUND

The field of data processing is technologically important to several industries, business organizations, and/or individuals.

Existing techniques for facilitating stimulating of muscles of users are deficient with regard to several aspects. For instance, current technologies do not capture the muscle activity of users accurately in real-time. Furthermore, current technologies do not facilitate remotely storing and sharing captured information associated with the muscles. Moreover, current technologies do not facilitate developing and implementing programs for muscle training.

Therefore, there is a need for methods, systems, apparatuses, and devices for facilitating stimulating of muscles of users that may overcome one or more of the above-mentioned problems and/or limitations.

BRIEF SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a method for facilitating stimulating of muscles of users, in accordance with some embodiments. The method may include a step of receiving, using a communication device, one or more muscle data from one or more sensors. Further, the one or more sensors may be configured for generating the one or more muscle data based on detecting a muscle activation of one or more muscles of one or more first users. Further, the method may include a step of analyzing, using a processing device, the one or more muscle data. Further, the method may include a step of generating, using the processing device, one or more first muscle activity data of the one or more muscles of the one or more first users based on the analyzing of the one or more muscle data. Further, the one or more first muscle activity data may include one or more first muscle activities of the one or more muscles of the one or more first users. Further, the method may include a step of receiving, using the communication device, one or more first biological metrics of the one or more first users from one or more first devices. Further, the method may include a step of receiving, using the communication device, one or more second biological metrics of one or more second users from one or more second devices. Further, the method may include a step of analyzing, using the processing device, the first muscle activity data, the one or more first biological metrics, and the one or more second biological metrics. Further, the method may include a step of transforming, using the processing device, the one or more first muscle activities into one or more second muscle activities of the one or more muscles of the one or more second users based on the analyzing of the first muscle activity data, the one or more first biological metrics, and the one or more second biological metrics. Further, the method may include a step of generating, using the processing device, one or more muscle activation commands for the muscle activation of the one or more muscles of the one or more second users based on the one or more second muscle activities. Further, the method may include a step of transmitting, using the communication device, the one or more muscle activation commands to one or more muscle stimulators disposable on the one or more body parts of the one or more second users. Further, the one or more muscle stimulators may be configured for stimulating the one or more muscles of the one or more second users based on the one or more muscle activation commands. Further, the stimulating may include the muscle activation of the one or more muscles of the one or more second users. Further, the method may include a step of storing, using a storage device, the first muscle activity data and the one or more muscle activation commands.

Further disclosed herein is a system for facilitating stimulating of muscles of users, in accordance with some embodiments. The system may include a communication device, a processing device, and a storage device. Further, the communication device may be configured for performing a step of receiving one or more muscle data from one or more sensors. Further, the one or more sensors may be configured for generating the one or more muscle data based on detecting a muscle activation of one or more muscles of one or more first users. Further, the communication device may be configured for performing a step of receiving one or more first biological metrics of the one or more first users from one or more first devices. Further, the communication device may be configured for performing a step of receiving one or more second biological metrics of one or more second users from one or more second devices. Further, the communication device may be configured for performing a step of transmitting one or more muscle activation commands to one or more muscle stimulators disposable on the one or more body parts of the one or more second users. Further, the one or more muscle stimulators is configured for stimulating the one or more muscles of the one or more second users based on the one or more muscle activation commands. Further, the stimulating may include the muscle activation of the one or more muscles of the one or more second users. The processing device may be communicatively coupled with the communication device. Further, the processing device may be configured for performing a step of analyzing the one or more muscle data. Further, the processing device may be configured for performing a step of generating one or more first muscle activity data of the one or more muscles of the one or more first users based on the analyzing of the one or more muscle data. Further, the one or more first muscle activity data may include one or more first muscle activities of the one or more muscles of the one or more first users. Further, the processing device may be configured for performing a step of analyzing the first muscle activity data, the one or more first biological metrics, and the one or more second biological metrics. Further, the processing device may be configured for performing a step of transforming the one or more first muscle activities into one or more second muscle activities of the one or more muscles of the one or more second users based on the analyzing of the first muscle activity data, the one or more first biological metrics, and the one or more second biological metrics. Further, the processing device may be configured for performing a step of generating the one or more muscle activation commands for the muscle activation of the one or more muscles of the one or more second users based on the one or more second muscle activities. The storage device may be communicatively coupled with the processing device. Further, the storage device may be configured for performing a step of storing the first muscle activity data and the one or more muscle activation commands.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION

Figure 1:
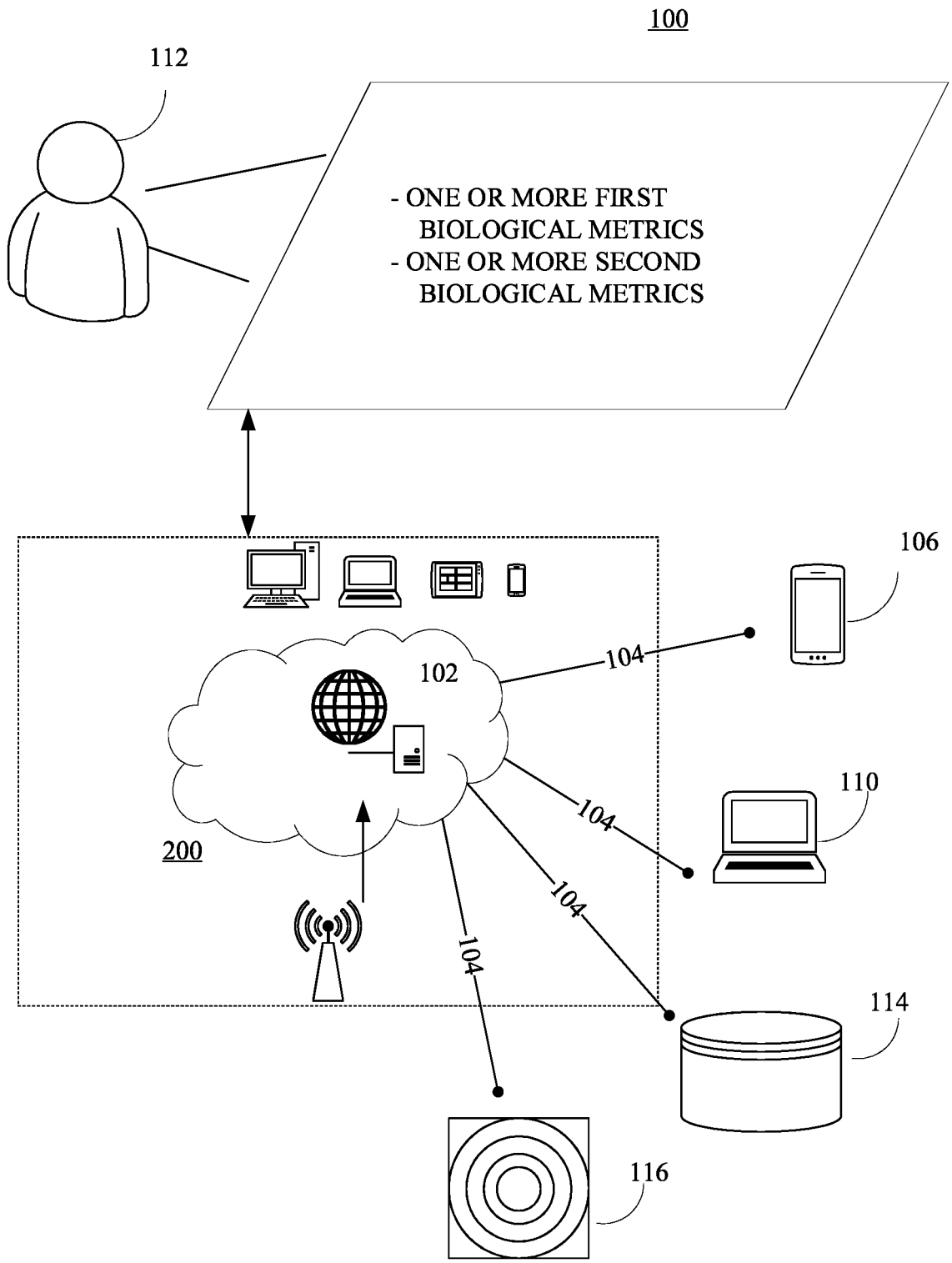
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of facilitating stimulating of muscles of users, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice-based interface, gesture-based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third-party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role-based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g. username, password, passphrase, PIN, secret question, secret answer etc.) and/or possession of a machine readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smart-card with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview:

The present disclosure describes methods, systems, apparatuses, and devices for facilitating stimulating of muscles of users.

The disclosed system may be configured for utilizing sensors to measure the muscle use of a user. Further, the disclosed system may be configured for converting the digital measurement (captured data) to an electronic signal and storing the captured data associated with a particular muscle.

When the muscle activity of the user exceeds an initially saved maximum, then that muscle activity may be collected as the new (100%) for that particular muscle.

Further, the disclosed system may be configured for converting the captured data to an electrical measurement or an amount of power of an electrical signal sent to a particular line to be connected to the particular muscle.

Further, the disclosed system may be configured for recording muscle usage during a given period. This usage may include working out, exercise, walking, or any activity where muscle usage patterns can be generated. The event may be saved under a retrievable name.

Further, each captured/monitored muscle and its sequence of use may be obtained and converted as an electrical measurement (or an electrical signal). This stored sequence of activity may then be shared with other users. The stored muscle usage data from the particular event may be shared with being a muscle stimulation digitally distributable program.

According to some embodiments, the disclosed system may be configured for generating specified programs. For example, a specific program may be provided for ACL reconstruction. Accordingly, various muscles and muscle groups that impact the ACL may be identified. Further, the user may choose a program such as walking, jogging (deep dive on time and depends on the runner selected), sprinting, and distance. Thereafter, based on the selected program, the sequence of muscle stimulation for each muscle may be provided.

Further, each muscle activity pattern is unique based on the origin and the specific activity. The disclosed system may capture and store the muscle patterns of users as they do certain activities. Each muscle activity may be stored and synced in the timeline, and the sequence may be played back. For example, the activity may include performing bench press and upper body work out. Accordingly, the user may select a workout, then the user may select time, then the system may display information about the muscles and the muscle groups being used, then the system may display level and compare it against the program owners. Further, the user may have an option to select a patch or line they want to adjust the power.

According to some embodiments, the disclosed system may be configured to perform real-time muscle capture and remote sharing.

According to some embodiments, the users may put their programs together based on their particular goals, similar to a playlist.

FIG. 1 is an illustration of an online platform 100 consistent with various embodiments of the present disclosure. By way of non-limiting example, the online platform 100 to enable facilitating stimulating of muscles of users may be hosted on a centralized server 102, such as, for example, a cloud computing service. The centralized server 102 may communicate with other network entities, such as, for example, a mobile device 106 (such as a smartphone, a laptop, a tablet computer, etc.), other electronic devices 110 (such as desktop computers, server computers, etc.), databases 114, and sensors 116 over a communication network 104, such as, but not limited to, the Internet. Further, users of the online platform 100 may include relevant parties such as, but not limited to, end-users, administrators, service providers, service consumers, and so on. Accordingly, in some instances, electronic devices operated by the one or more relevant parties may be in communication with the platform.

A user 112, such as the one or more relevant parties, may access online platform 100 through a web-based software application or browser. The web-based software application may be embodied as, for example, but not be limited to, a website, a web application, a desktop application, and a mobile application compatible with a computing device 200.

Figure 2:
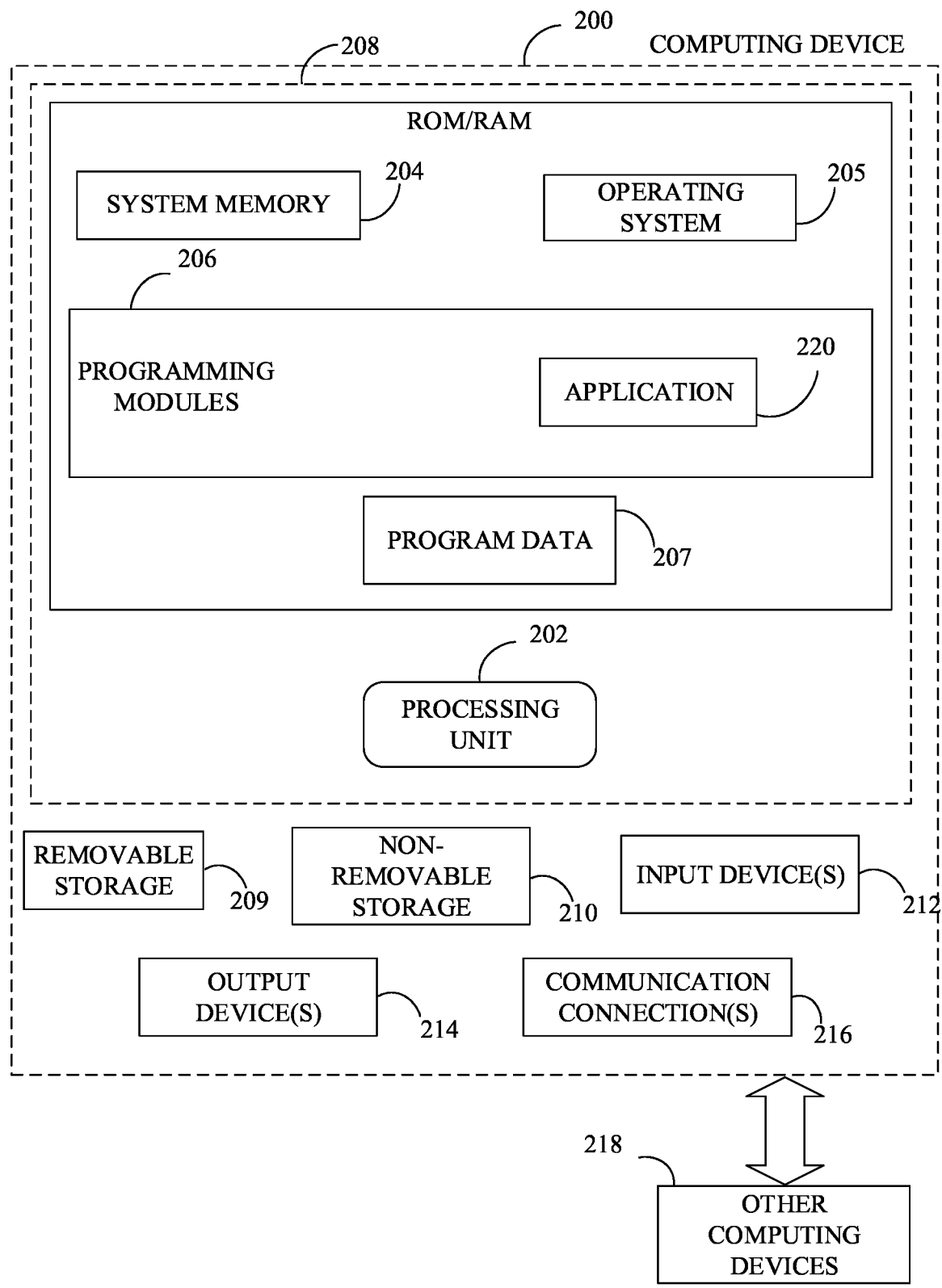
FIG. 2 is a block diagram of a computing device for implementing the methods disclosed herein, in accordance with some embodiments.

With reference to FIG. 2, a system consistent with an embodiment of the disclosure may include a computing device or cloud service, such as computing device 200. In a basic configuration, computing device 200 may include at least one processing unit 202 and a system memory 204. Depending on the configuration and type of computing device, system memory 204 may comprise, but is not limited to, volatile (e.g. random-access memory (RAM)), non-volatile (e.g. read-only memory (ROM)), flash memory, or any combination. System memory 204 may include operating system 205, one or more programming modules 206, and may include a program data 207. Operating system 205, for example, may be suitable for controlling computing device 200's operation. In one embodiment, programming modules 206 may include image-processing module, machine learning module. Furthermore, embodiments of the disclosure may be practiced in conjunction with a graphics library, other operating systems, or any other application program and is not limited to any particular application or system. This basic configuration is illustrated in FIG. 2 by those components within a dashed line 208.

Computing device 200 may have additional features or functionality. For example, computing device 200 may also include additional data storage devices (removable and/or non-removable) such as, for example, magnetic disks, optical disks, or tape. Such additional storage is illustrated in FIG. 2 by a removable storage 209 and a non-removable storage 210. Computer storage media may include volatile and non-volatile, removable and non-removable media implemented in any method or technology for storage of information, such as computer-readable instructions, data structures, program modules, or other data. System memory 204, removable storage 209, and non-removable storage 210 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 200. Any such computer storage media may be part of device 200. Computing device 200 may also have input device(s) 212 such as a keyboard, a mouse, a pen, a sound input device, a touch input device, a location sensor, a camera, a biometric sensor, etc. Output device(s) 214 such as a display, speakers, a printer, etc. may also be included. The aforementioned devices are examples and others may be used.

Computing device 200 may also contain a communication connection 216 that may allow device 200 to communicate with other computing devices 218, such as over a network in a distributed computing environment, for example, an intranet or the Internet. Communication connection 216 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 204, including operating system 205. While executing on processing unit 202, programming modules 206 (e.g., application 220 such as a media player) may perform processes including, for example, one or more stages of methods, algorithms, systems, applications, servers, databases as described above. The aforementioned process is an example, and processing unit 202 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Figure 3:
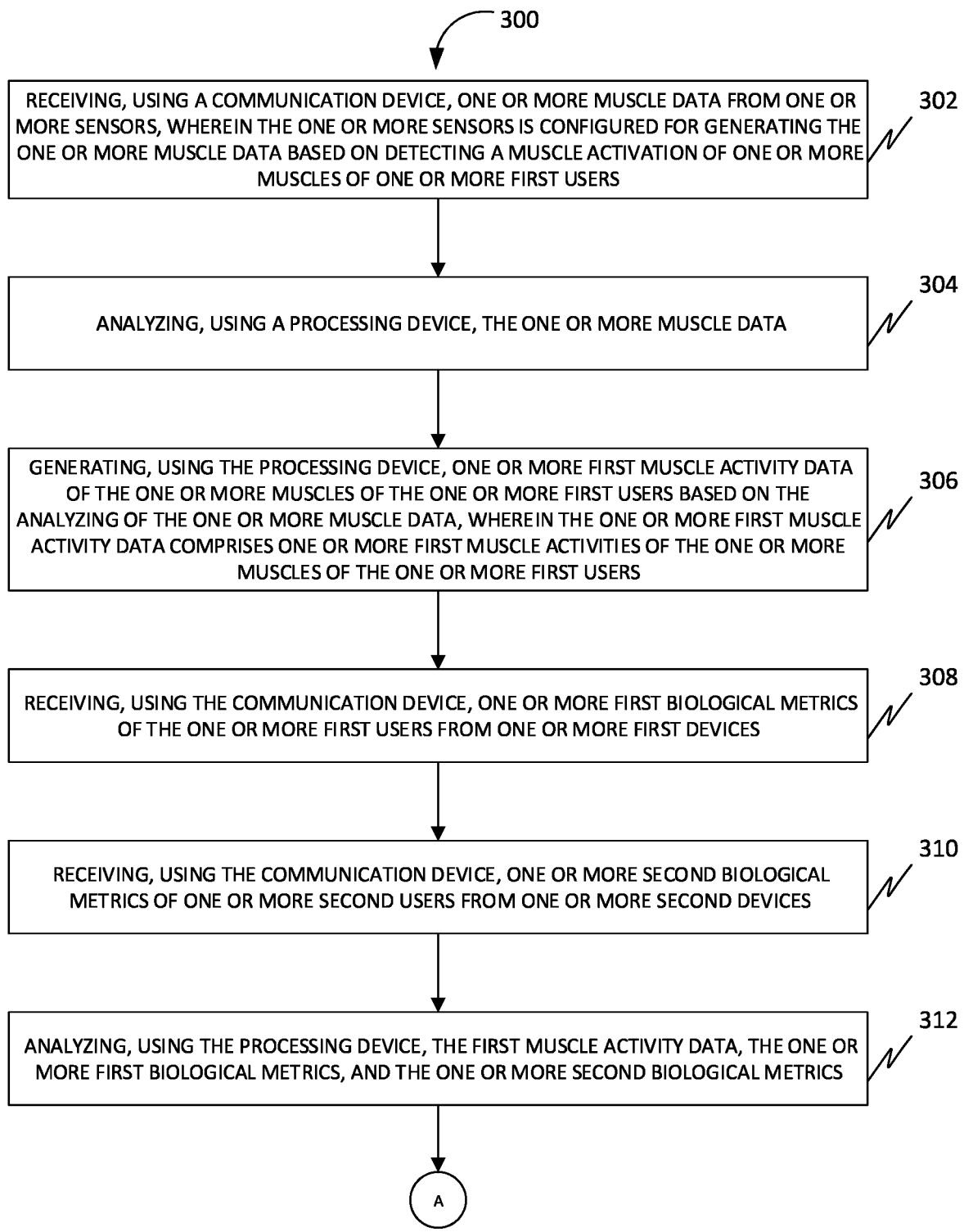
FIG. 3 is a flow chart of a method for facilitating stimulating of muscles of users, in accordance with some embodiments.

FIG. 3 is a flow chart of a method 300 for facilitating stimulating of muscles of users, in accordance with some embodiments.

Further, the method 300 may include a step 302 of receiving, using a communication device, one or more muscle data from one or more sensors. Further, the one or more sensors may be configured for generating the one or more muscle data based on detecting a muscle activation of one or more muscles of one or more first users.

Further, the method 300 may include a step 304 of analyzing, using a processing device, the one or more muscle data.

Further, the method 300 may include a step 306 of generating, using the processing device, one or more first muscle activity data of the one or more muscles of the one or more first users based on the analyzing of the one or more muscle data. Further, the one or more first muscle activity data may include one or more first muscle activities of the one or more muscles of the one or more first users.

Further, the method 300 may include a step 308 of receiving, using the communication device, one or more first biological metrics of the one or more first users from one or more first devices. Further, the one or more first biological metrics may include a heart rate, a respiration rate, a body temperature, a body weight, a body height, a body fat, a muscle mass, a stamina, a level of one or more hormones, a blood sugar, etc.

Further, the method 300 may include a step 310 of receiving, using the communication device, one or more second biological metrics of one or more second users from one or more second devices. Further, the one or more second biological metrics may include a heart rate, a respiration rate, a body temperature, a body weight, a body height, a body fat, a muscle mass, a stamina, a level of one or more hormones, a blood sugar, etc. Further, the method 300 may include a step 312 of analyzing, using the processing device, the first muscle activity data, the one or more first biological metrics, and the one or more second biological metrics.

Figure 4:
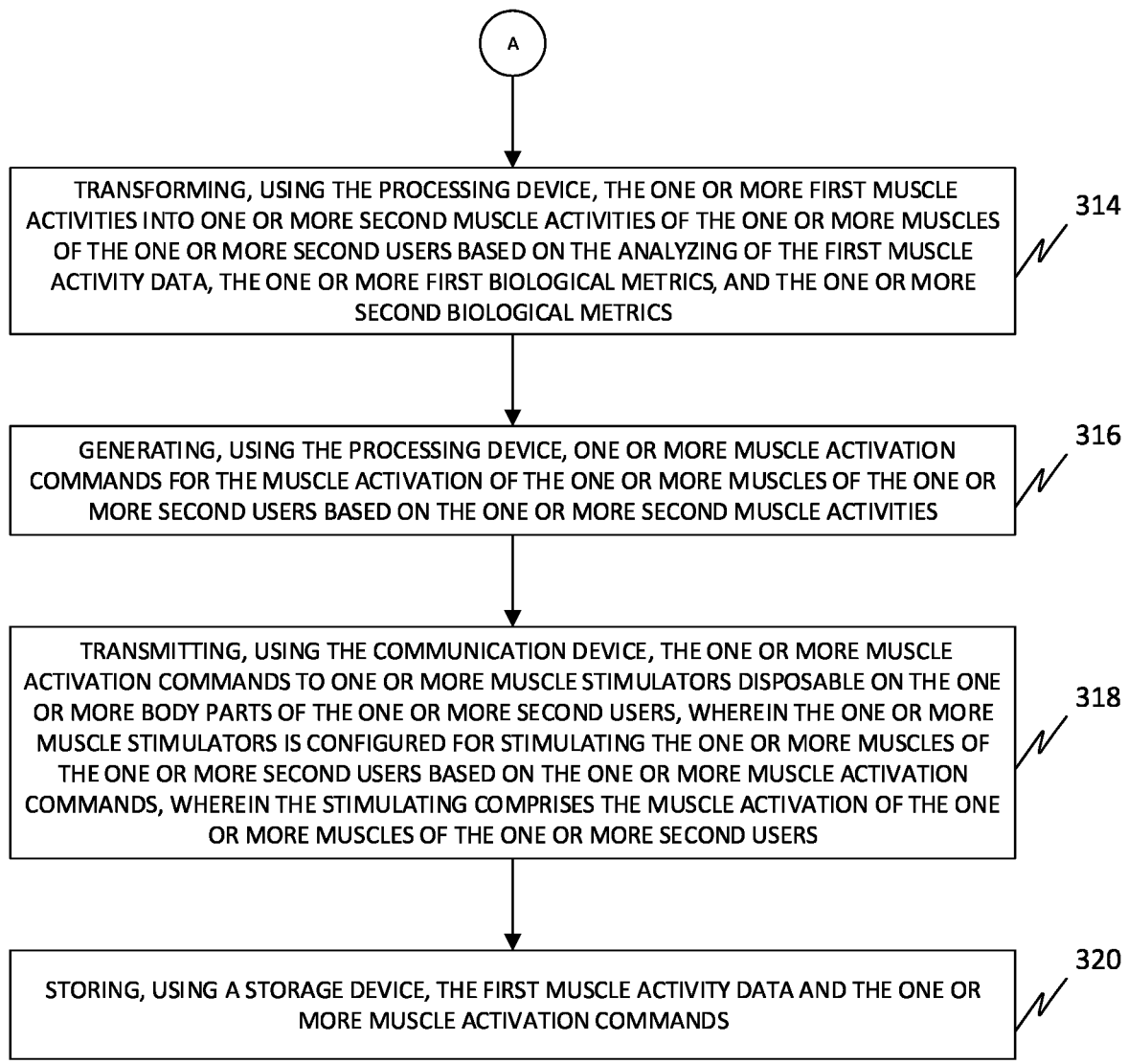
FIG. 4 is a continuation flow chart of FIG. 3.

FIG. 4 is a continuation flow chart of FIG. 3.

Further, the method 300 may include a step 314 of transforming, using the processing device, the one or more first muscle activities into one or more second muscle activities of the one or more muscles of the one or more second users based on the analyzing of the first muscle activity data, the one or more first biological metrics, and the one or more second biological metrics.

Further, the method 300 may include a step 316 of generating, using the processing device, one or more muscle activation commands for the muscle activation of the one or more muscles of the one or more second users based on the one or more second muscle activities.

Further, the method 300 may include a step 318 of transmitting, using the communication device, the one or more muscle activation commands to one or more muscle stimulators disposable on the one or more body parts of the one or more second users. Further, the one or more muscle stimulators may be configured for stimulating the one or more muscles of the one or more second users based on the one or more muscle activation commands. Further, the stimulating may include the muscle activation of the one or more muscles of the one or more second users.

Further, the method 300 may include a step 320 of storing, using a storage device, the first muscle activity data and the one or more muscle activation commands.

In some embodiments, the method 300 may include a step of receiving one or more muscle response data from one or more second sensors (one or more second sensors 814) associated with the one or more second users. Further, the one or more second sensors may be configured for generating the one or more muscle response data based on a muscle response of the one or more muscles of the one or more second users. Further, the one or more muscles of the one or more second users produce the muscle response based on the stimulating of the one or more muscles of the one or more second users. Further, the method 300 may include a step of analyzing the one or more muscle response data. Further, the generating of the one or more muscle activation commands for the muscle activation of the one or more muscles of the one or more second users may be further based on the analyzing of the one or more muscle response data. In an embodiment, the one or more second sensors may include one or more electromyography (EMG) sensors. Further, the one or more EMG sensors may be disposable on one or more body parts of the one or more second users. Further, the one or more EMG sensors may be configured for sensing an electrical activity of the one or more muscles of the one or more second users. Further, the detecting of the muscle response may be based on the sensing of the electrical activity. Further, the muscle response may include one or more of a muscle contraction and a muscle relaxation.

In further embodiments, the one or more muscles of the one or more first users may include one or more muscle groups corresponding to one or more body parts of the one or more first users. Further, the one or more muscle groups of the one or more first users may include chest muscles, back muscles, arm muscles, abdominal muscles, leg muscles, shoulder muscles, etc. Further, the one or more muscle groups of the one or more first users may include abdominals, biceps, deltoids, pectoral, obliques, trapezius, latissimus dorsi, erector spinae, etc. Further, the generating of the one or more muscle data of the one or more first users may be based on monitoring the one or more muscle groups of the one or more first users during one or more of one or more time duration and one or more user activities performed by the one or more first users. Further, the one or more user activities may include working out, exercise, walking, playing, dancing, swimming, biking, etc. Further, the exercise may include bench presses, lunges, pushups, squats, burpees, planks, etc. Further, the one or more time duration may include one or more seconds, one or more minutes, one or more hours, etc. Further, the one or more muscle data may include a multi track recording of the muscle activation of the one or more muscle groups of the one or more first users corresponding to one or more of the one or more time duration and the one or more user activities. Further, the muscle activation of the one or more muscle groups of the one or more first users may include one or more of a muscle contraction and a muscle relaxation of the one or more muscle groups of the one or more first users.

In further embodiments, the analyzing of the one or more muscle data may include analyzing the multi track recording of the muscle activation of the one or more muscle groups of the one or more first users corresponding to one or more of the one or more time duration and the one or more user activities. Further, the method 300 may include a step of determining one or more muscle activity parameters of the one or more muscle groups of the one or more first users corresponding to one or more of the one or more time duration and the one or more user activities based on the analyzing of the multi track recording of the muscle activation of the one or more muscle groups of the one or more first users. Further, the one or more muscle activity parameters may include an intensity of the muscle activation of the one or more muscle groups of the one or more first users, a pattern of the muscle activation of the one or more muscle groups of the one or more first users, etc. Further, the muscle activation may include one or more of a muscle contraction and a muscle relaxation. Further, the intensity of the muscle activation of the one or more muscle groups of the one or more first users may include an absolute intensity of the muscle activation of the one or more muscle groups of the one or more first users, a relative intensity of the muscle activation of the one or more muscle groups of the one or more first users, etc. Further, the relative intensity may include a current level of the muscle activation of the one or more muscle groups of the one or more first users expressed as a percentage of a maximum level of the muscle activation of the one or more muscle groups of the one or more first users. Further, the relative intensity may include a first level of the muscle activation of the one or more muscle groups of the one or more first users expressed as a percentage of a second level of the muscle activation of one or more first muscle groups of the one or more first users. Further, the generating of the one or more first muscle activity data of the one or more muscles of the one or more first users may be further based on the determining of the one or more muscle activity parameters of the one or more muscle groups of the one or more first users corresponding to one or more of the one or more time duration and the one or more user activities.

In further embodiments, the one or more first muscle activity data may include a muscle activity profile of the one or more muscles of the one or more first users. Further, the muscle activity profile may include one or more activation patterns of the muscle activation of the one or more muscle groups of the one or more first users, one or more activation intensity of the one or more muscle groups of the one or more first users, one or more activation duration of the one or more muscle groups of the one or more first users, etc. Further, the one or more activation patterns may include a sequence of the muscle activation of the one or more muscle groups of the one or more first users. Further, the one or more activation intensity may include a level of the muscle activation of the one or more muscles of the one or more first users. Further, the one or more activation duration may include a duration of the muscle activation of the one or more muscles of the one or more first users. Further, the generating of the one or more first muscle activity data may include generating the muscle activity profile of the one or more muscles of the one or more first users based on the determining of the one or more muscle activity parameters of the one or more muscle groups of the one or more first users corresponding to one or more of the one or more time duration and the one or more user activities.

In some embodiments, the detecting of the muscle activation of the one or more muscles of the one or more first users may include detecting the muscle activation of the one or more muscles of the one or more first users during one or more user activities performed by the one or more first users. Further, the one or more user activities may include working out, exercise, walking, playing, dancing, swimming, biking, etc. Further, the exercise may include bench presses, lunges, pushups, squats, burpees, planks, etc. Further, the one or more first muscle activity data may include the one or more first muscle activities corresponding to the one or more user activities performed by the one or more first users. Further, the one or more muscle activation commands may correspond to the one or more user activities.

In some embodiments, the one or more sensors may include one or more mechanomyogram (MMG) sensors. Further, the one or more MMG sensors may be disposable on one or more body parts of the one or more first users. Further, the one or more MMG sensors may be configured for sensing a mechanical activity of the one or more muscles of the one or more first users. Further, the detecting of the muscle activation may be based on the sensing of the mechanical activity.

In some embodiments, the one or more sensors may include one or more thermal sensors. Further, the one or more thermal sensors may be configured for sensing a thermal activity of the one or more muscles of the one or more first users. Further, the detecting of the muscle activation may be based on the sensing of the thermal activity.

In some embodiments, the one or more sensors may include one or more electromyography (EMG) sensors. Further, the one or more EMG sensors may be disposable on one or more body parts of the one or more first users. Further, the one or more EMG sensors may be configured for sensing an electrical activity of the one or more muscles of the one or more first users. Further, the detecting of the muscle activation may be based on the sensing of the electrical activity.

In some embodiments, the one or more second user devices may include one or more second biological sensors. Further, the one or more second biological sensors may be configured for generating the one or more second biological metrics based on measuring one or more of a physical parameter and a physiological parameter of a body of the one or more second users.

In some embodiments, the one or more first user devices may include one or more first biological sensors. Further, the one or more first biological sensors may be configured for generating the one or more first biological metrics based on measuring one or more of a physical parameter and a physiological parameter of a body of the one or more first users.

Figure 5:
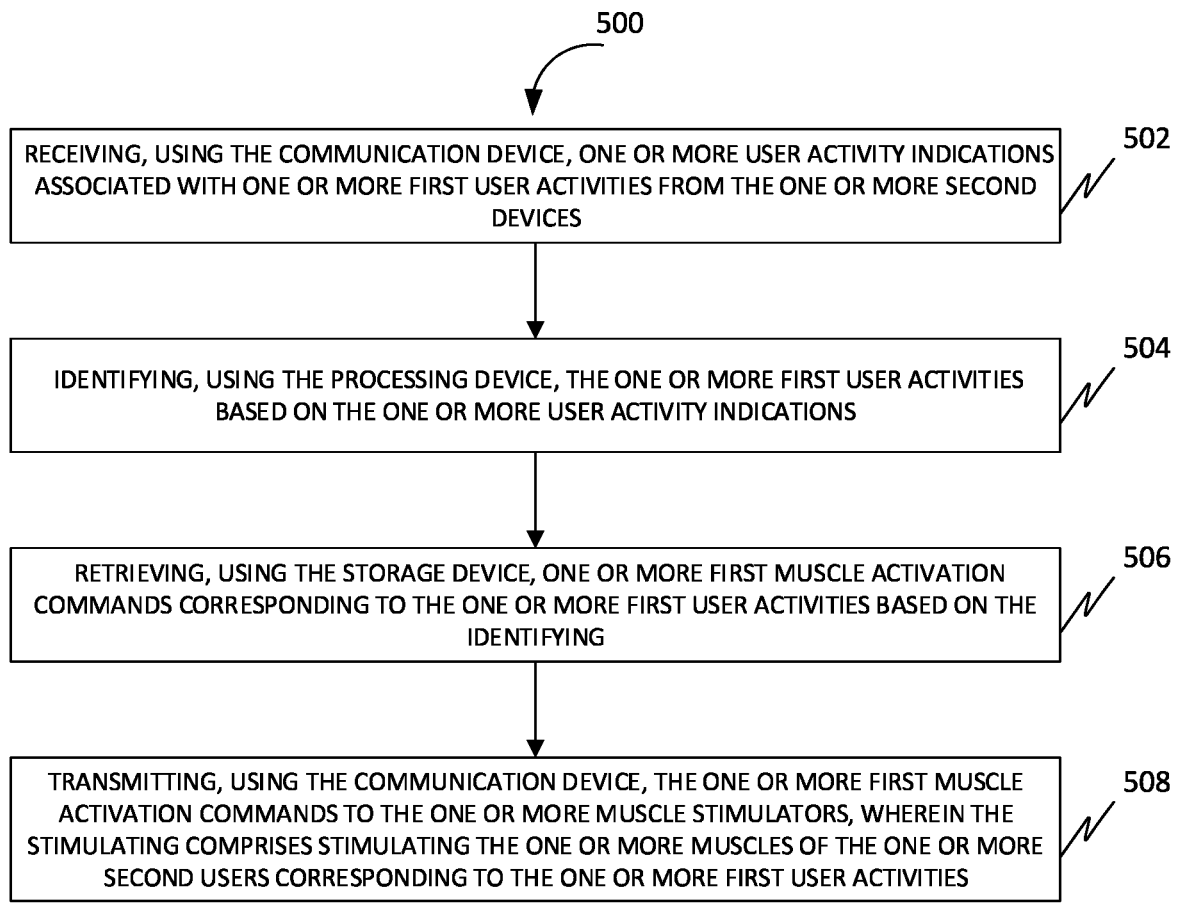
FIG. 5 is a flow chart of the method for facilitating stimulating of muscles of users in which the method further may include transmitting the one or more first muscle activation commands to the one or more muscle stimulators, in accordance with some embodiments.

FIG. 5 is a flow chart of a method 500 for facilitating stimulating of muscles of users in which the method 500 further may include transmitting the one or more first muscle activation commands to the one or more muscle stimulators, in accordance with some embodiments. Further, at 502, the method 500 may include receiving, using the communication device, one or more user activity indications associated with one or more first user activities from the one or more second devices. Further, at 504, the method 500 may include identifying, using the processing device, the one or more first user activities based on the one or more user activity indications. Further, at 506, the method 500 may include retrieving, using the storage device, one or more first muscle activation commands corresponding to the one or more first user activities based on the identifying. Further, at 508, the method 500 may include transmitting, using the communication device, the one or more first muscle activation commands to the one or more muscle stimulators. Further, the stimulating may include stimulating the one or more muscles of the one or more second users corresponding to the one or more first user activities.

Figure 6:
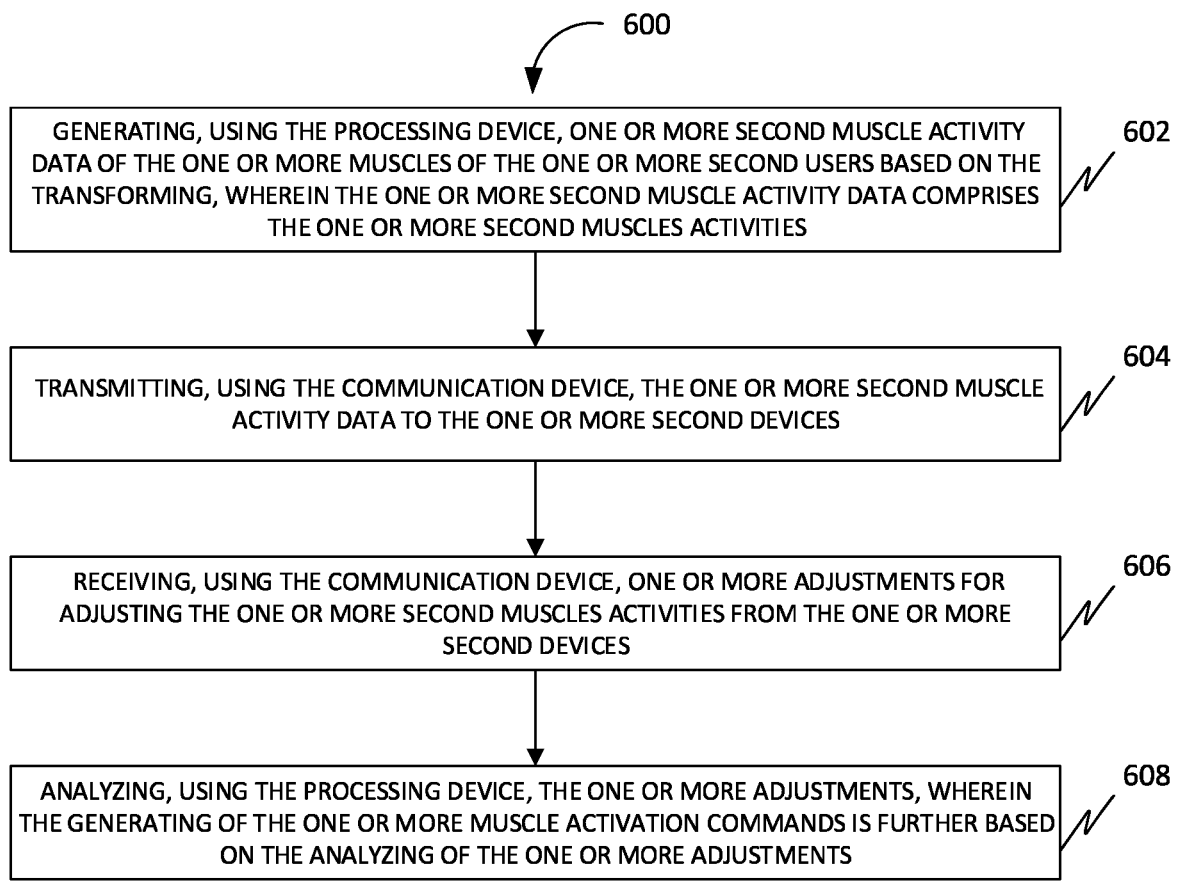
FIG. 6 is the flow chart of the method for facilitating stimulating of muscles of users in which the method further may include analyzing the one or more adjustments, in accordance with some embodiments.

FIG. 6 is a flow chart of a method 600 for facilitating stimulating of muscles of users in which the method 600 further may include analyzing the one or more adjustments, in accordance with some embodiments. Further, at 602, the method 600 may include generating, using the processing device, one or more second muscle activity data of the one or more muscles of the one or more second users based on the transforming. Further, the one or more second muscle activity data may include the one or more second muscles activities. Further, at 604, the method 600 may include transmitting, using the communication device, the one or more second muscle activity data to the one or more second devices. Further, at 606, the method 600 may include receiving, using the communication device, one or more adjustments for adjusting the one or more second muscles activities from the one or more second devices. Further, at 608, the method 600 may include analyzing, using the processing device, the one or more adjustments. Further, the generating of the one or more muscle activation commands may be based on the analyzing of the one or more adjustments.

In some embodiments, the one or more first muscles activities may include a sequence of muscle activation of the one or more muscles of the one or more first users and a strength of muscle activation of the one or more muscles of the one or more first users. Further, the one or more second muscles activities may include the sequence of muscle activation of the one or more muscles of the one or more second users and the strength of muscle activation of the one or more muscles of the one or more second users.

Figure 7:
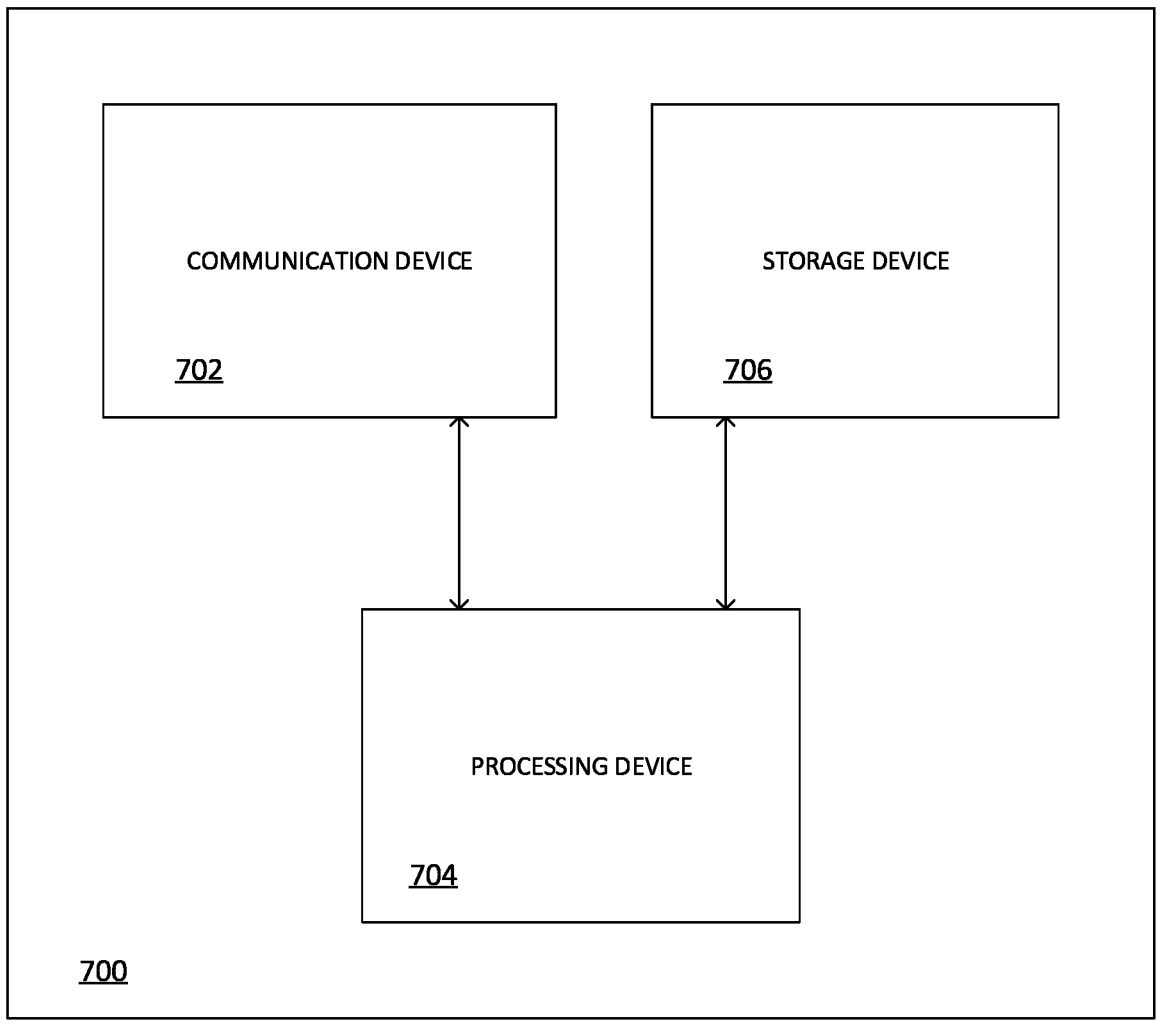
FIG. 7 is a block diagram of a system for facilitating stimulating of muscles of users, in accordance with some embodiments.

FIG. 7 is a block diagram of a system 700 for facilitating stimulating of muscles of users, in accordance with some embodiments. The system 700 may include a communication device 702, a processing device 704, and a storage device 706.

Further, the communication device 702 may be configured for performing a step of receiving one or more muscle data from one or more sensors. Further, the one or more sensors may be configured for generating the one or more muscle data based on detecting a muscle activation of one or more muscles of the one or more first users.

Further, the communication device 702 may be configured for performing a step of receiving one or more first biological metrics of the one or more first users from one or more first devices.

Further, the communication device 702 may be configured for performing a step of receiving one or more second biological metrics of one or more second users from one or more second devices.

Further, the communication device 702 may be configured for performing a step of transmitting one or more muscle activation commands to one or more muscle stimulators disposable on the one or more body parts of the one or more second users. Further, the one or more muscle stimulators may be configured for stimulating the one or more muscles of the one or more second users based on the one or more muscle activation commands. Further, the stimulating may include the muscle activation of the one or more muscles of the one or more second users.

The processing device 704 may be communicatively coupled with the communication device 702.

Further, the processing device 704 may be configured for performing a step of analyzing the one or more muscle data.

Further, the processing device 704 may be configured for performing a step of generating one or more first muscle activity data of the one or more muscles of the one or more first users based on the analyzing of the one or more muscle data. Further, the one or more first muscle activity data may include one or more first muscle activities of the one or more muscles of the one or more first users.

Further, the processing device 704 may be configured for performing a step of analyzing the first muscle activity data, the one or more first biological metrics, and the one or more second biological metrics.

Further, the processing device 704 may be configured for performing a step of transforming the one or more first muscle activities into one or more second muscle activities of the one or more muscles of the one or more second users based on the analyzing of the first muscle activity data, the one or more first biological metrics, and the one or more second biological metrics.

Further, the processing device 704 may be configured for performing a step of generating the one or more muscle activation commands for the muscle activation of the one or more muscles of the one or more second users based on the one or more second muscle activities.

The storage device 706 may be communicatively coupled with the processing device 704.

Further, the storage device 706 may be configured for performing a step of storing the first muscle activity data and the one or more muscle activation commands.

In some embodiments, the communication device 702 may be configured for performing a step of receiving one or more muscle response data from one or more second sensors (one or more second sensors 814) associated with the one or more second users. Further, the one or more second sensors may be configured for generating the one or more muscle response data based on a muscle response of the one or more muscles of the one or more second users. Further, the one or more muscles of the one or more second users produce the muscle response based on the stimulating of the one or more muscles of the one or more second users. Further, the processing device 704 may be configured for performing a step of analyzing the one or more muscle response data. Further, the generating of the one or more muscle activation commands for the muscle activation of the one or more muscles of the one or more second users may be further based on the analyzing of the one or more muscle response data. In an embodiment, the one or more second sensors may include one or more electromyography (EMG) sensors. Further, the one or more EMG sensors may be disposable on one or more body parts of the one or more second users. Further, the one or more EMG sensors may be configured for sensing an electrical activity of the one or more muscles of the one or more second users. Further, the detecting of the muscle response may be based on the sensing of the electrical activity. Further, the muscle response may include one or more of a muscle contraction and a muscle relaxation.

In further embodiments, the one or more muscles of the one or more first users may include one or more muscle groups corresponding to one or more body parts of the one or more first users. Further, the one or more muscle groups of the one or more first users may include chest muscles, back muscles, arm muscles, abdominal muscles, leg muscles, shoulder muscles, etc. Further, the one or more muscle groups of the one or more first users may include abdominals, biceps, deltoids, pectoral, obliques, trapezius, latissimus dorsi, erector spinae, etc. Further, the generating of the one or more muscle data of the one or more first users may be based on monitoring the one or more muscle groups of the one or more first users during one or more of one or more time duration and one or more user activities performed by the one or more first users. Further, the one or more user activities may include working out, exercise, walking, playing, dancing, swimming, biking, etc. Further, the exercise may include bench presses, lunges, pushups, squats, burpees, planks, etc. Further, the one or more time duration may include one or more seconds, one or more minutes, one or more hours, etc. Further, the one or more muscle data may include a multi track recording of the muscle activation of the one or more muscle groups of the one or more first users corresponding to one or more of the one or more time duration and the one or more user activities. Further, the muscle activation of the one or more muscle groups of the one or more first users may include one or more of a muscle contraction and a muscle relaxation of the one or more muscle groups of the one or more first users.

In further embodiments, the analyzing of the one or more muscle data may include analyzing the multi track recording of the muscle activation of the one or more muscle groups of the one or more first users corresponding to one or more of the one or more time duration and the one or more user activities. Further, the processing device 704 may be configured for performing a step of determining one or more muscle activity parameters of the one or more muscle groups of the one or more first users corresponding to one or more of the one or more time duration and the one or more user activities based on the analyzing of the multi track recording of the muscle activation of the one or more muscle groups of the one or more first users. Further, the one or more muscle activity parameters may include an intensity of the muscle activation of the one or more muscle groups of the one or more first users, a pattern of the muscle activation of the one or more muscle groups of the one or more first users, etc. Further, the muscle activation may include one or more of a muscle contraction and a muscle relaxation. Further, the intensity of the muscle activation of the one or more muscle groups of the one or more first users may include an absolute intensity of the muscle activation of the one or more muscle groups of the one or more first users, a relative intensity of the muscle activation of the one or more muscle groups of the one or more first users, etc. Further, the relative intensity may include a current level of the muscle activation of the one or more muscle groups of the one or more first users expressed as a percentage of a maximum level of the muscle activation of the one or more muscle groups of the one or more first users. Further, the relative intensity may include a first level of the muscle activation of the one or more muscle groups of the one or more first users expressed as a percentage of a second level of the muscle activation of one or more first muscle groups of the one or more first users. Further, the generating of the one or more first muscle activity data of the one or more muscles of the one or more first users may be further based on the determining of the one or more muscle activity parameters of the one or more muscle groups of the one or more first users corresponding to one or more of the one or more time duration and the one or more user activities.

In further embodiments, the one or more first muscle activity data may include a muscle activity profile of the one or more muscles of the one or more first users. Further, the muscle activity profile may include one or more activation patterns of the muscle activation of the one or more muscle groups of the one or more first users, one or more activation intensity of the one or more muscle groups of the one or more first users, one or more activation duration of the one or more muscle groups of the one or more first users, etc. Further, the one or more activation patterns may include a sequence of the muscle activation of the one or more muscle groups of the one or more first users. Further, the one or more activation intensity may include a level of the muscle activation of the one or more muscles of the one or more first users. Further, the one or more activation duration may include a duration of the muscle activation of the one or more muscles of the one or more first users. Further, the generating of the one or more first muscle activity data may include generating the muscle activity profile of the one or more muscles of the one or more first users based on the determining of the one or more muscle activity parameters of the one or more muscle groups of the one or more first users corresponding to one or more of the one or more time duration and the one or more user activities.

In some embodiments, the detecting of the muscle activation of the one or more muscles of the one or more first users may include detecting the muscle activation of the one or more muscles of the one or more first users during one or more user activities performed by the one or more first users. Further, the one or more first muscle activity data may include the one or more first muscle activities corresponding to the one or more user activities performed by the one or more first users. Further, the one or more muscle activation commands may correspond to the one or more user activities.

In some embodiments, the one or more sensors may include one or more mechanomyogram (MMG) sensors. Further, the one or more MMG sensors may be disposable on one or more body parts of the one or more first users. Further, the one or more MMG sensors may be configured for sensing a mechanical activity of the one or more muscles of the one or more first users. Further, the detecting of the muscle activation may be based on the sensing of the mechanical activity.

In some embodiments, the one or more sensors may include one or more thermal sensors. Further, the one or more thermal sensors may be configured for sensing a thermal activity of the one or more muscles of the one or more first users. Further, the detecting of the muscle activation may be based on the sensing of the thermal activity.

In some embodiments, the one or more sensors may include one or more electromyography (EMG) sensors. Further, the one or more EMG sensors may be disposable on one or more body parts of the one or more first users. Further, the one or more EMG sensors may be configured for sensing an electrical activity of the one or more muscles of the one or more first users. Further, the detecting of the muscle activation may be based on the sensing of the electrical activity.

In some embodiments, the one or more second user devices may include one or more second biological sensors. Further, the one or more second biological sensors may be configured for generating the one or more second biological metrics based on measuring one or more of a physical parameter and a physiological parameter of a body of the one or more second users.

In some embodiments, the one or more first user devices may include one or more first biological sensors. Further, the one or more first biological sensors may be configured for generating the one or more first biological metrics based on measuring one or more of a physical parameter and a physiological parameter of a body of the one or more first users.

In some embodiments, the communication device 702 may be configured for performing a step of receiving one or more user activity indications associated with one or more first user activities from the one or more second devices. Further, the communication device 702 may be configured for performing a step of transmitting one or more first muscle activation commands to the one or more muscle stimulators. Further, the stimulating may include stimulating the one or more muscles of the one or more second users corresponding to the one or more first user activities. Further, the processing device 704 may be configured for performing a step of identifying the one or more first user activities based on the one or more user activity indications. Further, the storage device 706 may be configured for performing a step of retrieving the one or more first muscle activation commands corresponding to the one or more first user activities based on the identifying.

In some embodiments, the communication device 702 may be configured for performing a step of transmitting one or more second muscle activity data to the one or more second devices. Further, the communication device 702 may be configured for performing a step of receiving one or more adjustments for adjusting the one or more second muscles activities from the one or more second devices. Further, the processing device 704 may be configured for performing a step of generating the one or more second muscle activity data of the one or more muscles of the one or more second users based on the transforming. Further, the one or more second muscle activity data may include the one or more second muscles activities. Further, the processing device 704 may be configured for performing a step of analyzing the one or more adjustments. Further, the generating of the one or more muscle activation commands may be based on the analyzing of the one or more adjustments.

In some embodiments, the one or more first muscles activities may include a sequence of muscle activation of the one or more muscles of the one or more first users and a strength of muscle activation of the one or more muscles of the one or more first users. Further, the one or more second muscles activities may include the sequence of muscle activation of the one or more muscles of the one or more second users and the strength of muscle activation of the one or more muscles of the one or more second users.

Figure 8:
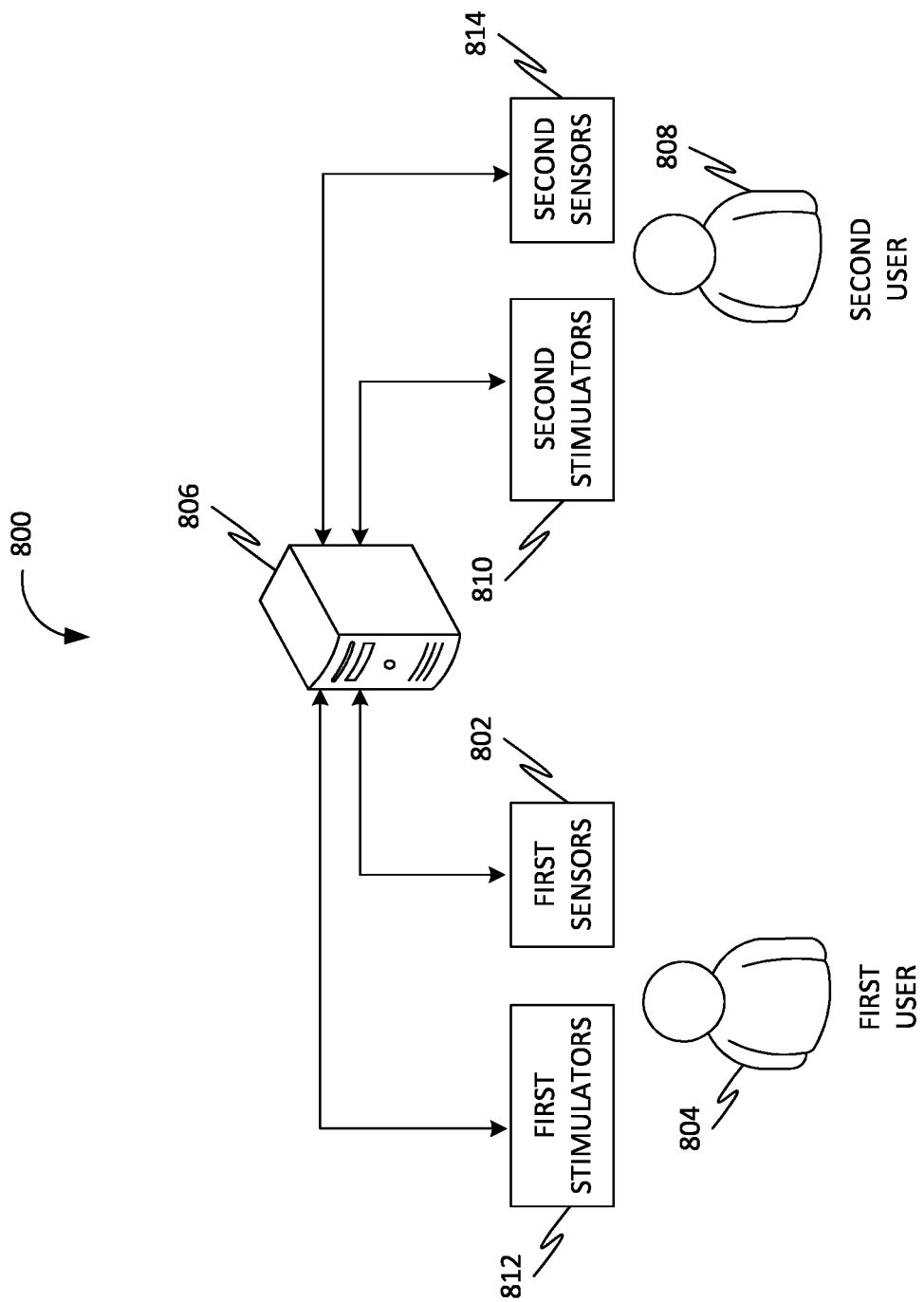
FIG. 8 is a schematic of a system for muscle pattern storage and distribution for facilitating stimulating of muscles of users, in accordance with some embodiments.

FIG. 8 is a schematic of a system 800 for muscle pattern storage and distribution for facilitating stimulating of muscles of users, in accordance with some embodiments. Further, the system 800 may include one or more first sensors 802, one or more first stimulators 812, one or more second stimulators 810, one or more second sensors 814, and a computing device 806. Further, the one or more first sensors 802 may be disposed on a first user 804 to capture muscle activation of the first user 804. Further, the one or more first stimulators 812 may be disposed on the first user 804. Further, the capturing may be performed by one or more EMG sensors (such as the one or more first sensors 802) placed over the corresponding one or more muscles of the first user 804. In some instances, the one or more first sensors 802 may be disposed on a suit worn by the first user 804. Further, the capturing may include obtaining one or more of the intensities of the muscle activation of the first user 804, which muscles have been activated, the sequence of activated muscles and the duration of activation. In addition to the muscle activation/contraction data, other factors may be captured such as physical/physiological parameters of the first user 804 and a second user 808. Further, first captured data of the first user 804 (or the muscle activation/contraction data) may be converted to electronic signals which are sent to the computing device 806 for storage. Further, the computing device 806 may be configured to translate/transform the first captured data to generate first transformed data based on the additional factors associated with one or both of the first user 804 and the second user 808. In most cases, the first user 804 and the second user 808 may be distinct on several counts (e.g. weight, muscle mass, stamina, etc.). The first translated/transformed captured data may be suitable for the second user 808.

Thereafter, the first transformed captured data may be applied onto the one or more second stimulators 810 (muscle stimulators) disposed on the body of the second user 808 to replicate the muscle activation of the first user 804.

Further, in some embodiments, the one or more second sensors 814 may be disposed on the second user 808 to capture muscle activation of the second user 808. Further, the capturing may be performed by the one or more EMG sensors (such as the one or more second sensors 814) placed over the corresponding one or more muscles of the second user 808. In some instances, the one or more second sensors 814 may be disposed on a suit worn by the second user 808. Further, the capturing may include obtaining one or more of the intensities of the muscle activation of the second user 808, which muscles have been activated, the sequence of activated muscles and the duration of activation. Further, second captured data of the second user 808 (or the muscle activation/contraction data) may be converted to electronic signals which are sent to the computing device 806 for storage. Further, the computing device 806 may be configured to translate/transform the second captured data to generate second transformed data based on the additional factors associated with one or both of the first user 804 and the second user 808. The second translated/transformed captured data may be suitable for the first user 804. Thereafter, the second transformed captured data may be applied onto the one or more first stimulators 812 (muscle stimulators) disposed on the body of the first user 804 to replicate the muscle activation of the second user 808.

Figure 9:
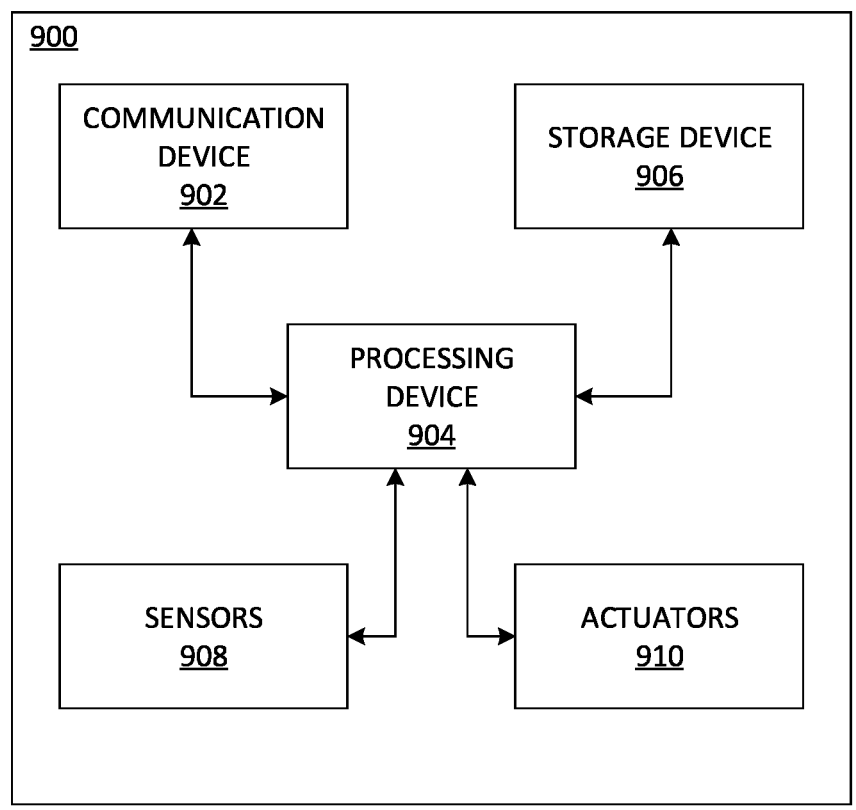
FIG. 9 is a block diagram of a system for muscle pattern storage and distribution for facilitating stimulating of muscles of users, in accordance with some embodiments.

FIG. 9 is a block diagram of a system 900 for muscle pattern storage and distribution for facilitating stimulating of muscles of users, in accordance with some embodiments.

Further, the system 900 may include a communication device 902, a processing device 904, a storage device 906, sensors 908, and actuators 910. Further, the communication device 902 may be communicatively coupled with the processing device 904. Further, the processing device 904 may be communicatively coupled with the storage device 906.

The sensors 908 may include EMG sensors placed over the corresponding one or more muscles of a user A. Further, the sensors 908 may be configured to capture one or more of which muscles have been activated, the intensity of the activation, the sequence of activated muscles and the duration of activation.

In addition to the muscle activation/contraction data, other factors may be captured as well (e.g. Physical/physiological parameters of the user A) by the sensors 908.

Further, the sensors 908 may be configured to convert the captured data to electronic signals.

Further, the communication device 902 may be configured to obtain the captured data from the sensors 908.

Further, the processing device 904 may be configured to translate/transform the captured data based on the additional factors associated with one or both the user A and a user B. In most cases the user A and the user B may be distinct on several counts (e.g. weight, muscle mass, stamina, etc.). The translated/transformed captured data would be suitable for the user B.

Further, the storage device 906 may be configured to store at least one of the captured data by the sensors 908 and the translated/transformed captured data.

Further, the communication device 902 may be configured to send the translated/transformed captured data to the actuators 910.

The actuators 910 may include muscle stimulators disposed on a user B's body to replicate the muscle activation.

Figure 10:
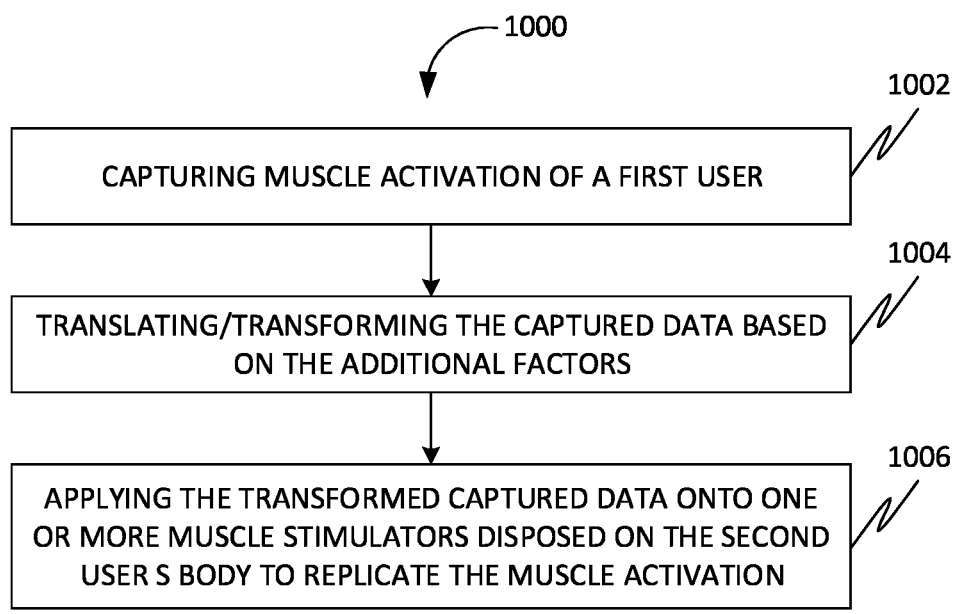
FIG. 10 is a flowchart of a method for facilitating muscle pattern storage and distribution, in accordance with some embodiments.

FIG. 10 is a flowchart of a method 1000 for facilitating muscle pattern storage and distribution, in accordance with some embodiments.

Further, at 1002, the method 1000 may include capturing muscle activation of a first user (a user A. The muscle activation may be captured via one or more sensors such as EMG sensors placed over the corresponding one or more muscles of the user A.

Further, at 1004, the method 1000 may include translating/transforming the captured data based on additional factors. The additional factors may be associated with one or both the user A and a user B. In most cases, the user A and the user B may be distinct on several counts (e.g. weight, muscle mass, stamina, etc.). The translated/transformed captured data would be suitable for the user B.

Further, at 1006, the method 1000 may include applying the transformed captured data onto one or more muscle stimulators disposed on the second user's body (user B's body to replicate the muscle activation.

Although the present disclosure has been explained in relation to its preferred embodiment, it is to be understood that many other possible modifications and variations can be made without departing from the spirit and scope of the disclosure.

I claim:

1. A method for facilitating stimulating of muscles of users, the method comprising:
    receiving, using a communication device, one or more muscle data from one or more sensors, wherein the one or more sensors is configured for generating the one or more muscle data based on detecting a muscle activation of one or more muscles of one or more first users, wherein the one or more sensors comprises one or more thermal sensors, wherein the one or more thermal sensors is configured for sensing a thermal activity of the one or more muscles of the one or more first users, wherein the detecting of the muscle activation is based on the sensing of the thermal activity;
    analyzing, using a processing device, the one or more muscle data;
    generating, using the processing device, one or more first muscle activity data of the one or more muscles of the one or more first users based on the analyzing of the one or more muscle data, wherein the one or more first muscle activity data comprises one or more first muscle activities of the one or more muscles of the one or more first users;
    receiving, using the communication device, one or more first biological metrics of the one or more first users from one or more first devices;
    receiving, using the communication device, one or more second biological metrics of one or more second users from one or more second devices;
    analyzing, using the processing device, the first muscle activity data, the one or more first biological metrics, and the one or more second biological metrics;
    transforming, using the processing device, the one or more first muscle activities into one or more second muscle activities of the one or more muscles of the one or more second users based on the analyzing of the first muscle activity data, the one or more first biological metrics, and the one or more second biological metrics;
    generating, using the processing device, one or more muscle activation commands for the muscle activation of the one or more muscles of the one or more second users based on the one or more second muscle activities;
    transmitting, using the communication device, the one or more muscle activation commands to one or more muscle stimulators disposable on the one or more body parts of the one or more second users, wherein the one or more muscle stimulators is configured for stimulating the one or more muscles of the one or more second users based on the one or more muscle activation commands, wherein the stimulating comprises the muscle activation of the one or more muscles of the one or more second users; and
    storing, using a storage device, the first muscle activity data and the one or more muscle activation commands.

2. The method of claim 1, wherein the one or more first user devices comprises one or more first biological sensors, wherein the one or more first biological sensors is configured for generating the one or more first biological metrics based on measuring one or more of a physical parameter and a physiological parameter of a body of the one or more first users.

3. The method of claim 1, wherein the one or more second user devices comprises one or more second biological sensors, wherein the one or more second biological sensors is configured for generating the one or more second biological metrics based on measuring one or more of a physical parameter and a physiological parameter of a body of the one or more second users.

4. The method of claim 1, wherein the one or more sensors comprises one or more electromyography (EMG) sensors, wherein the one or more EMG sensors is disposable on one or more body parts of the one or more first users, wherein the one or more EMG sensors is configured for sensing an electrical activity of the one or more muscles of the one or more first users, wherein the detecting of the muscle activation is based on the sensing of the electrical activity.

5. The method of claim 1, wherein the one or more sensors comprises one or more mechanomyogram (MMG) sensors, wherein the one or more MMG sensors is disposable on one or more body parts of the one or more first users, wherein the one or more MMG sensors is configured for sensing a mechanical activity of the one or more muscles of the one or more first users, wherein the detecting of the muscle activation is based on the sensing of the mechanical activity.

6. The method of claim 1, wherein the detecting of the muscle activation of the one or more muscles of the one or more first users comprises detecting the muscle activation of the one or more muscles of the one or more first users during one or more user activities performed by the one or more first users, wherein the one or more first muscle activity data comprises the one or more first muscle activities corresponding to the one or more user activities performed by the one or more first users, wherein the one or more muscle activation commands corresponds to the one or more user activities.

7. The method of claim 6 further comprising:
receiving, using the communication device, one or more user activity indications associated with one or more first user activities from the one or more second devices;
identifying, using the processing device, the one or more first user activities based on the one or more user activity indications;
retrieving, using the storage device, one or more first muscle activation commands corresponding to the one or more first user activities based on the identifying; and
transmitting, using the communication device, the one or more first muscle activation commands to the one or more muscle stimulators, wherein the stimulating comprises stimulating the one or more muscles of the one or more second users corresponding to the one or more first user activities.

8. The method of claim 1 further comprising:
generating, using the processing device, one or more second muscle activity data of the one or more muscles of the one or more second users based on the transforming, wherein the one or more second muscle activity data comprises the one or more second muscles activities;
transmitting, using the communication device, the one or more second muscle activity data to the one or more second devices;
receiving, using the communication device, one or more adjustments for adjusting the one or more second muscles activities from the one or more second devices; and
analyzing, using the processing device, the one or more adjustments, wherein the generating of the one or more muscle activation commands is further based on the analyzing of the one or more adjustments.

9. The method of claim 1, wherein the one or more first muscles activities comprises a sequence of muscle activation of the one or more muscles of the one or more first users and a strength of muscle activation of the one or more muscles of the one or more first users, wherein the one or more second muscles activities comprises the sequence of muscle activation of the one or more muscles of the one or more second users and the strength of muscle activation of the one or more muscles of the one or more second users.

10. A system for facilitating stimulating of muscles of users, the system comprising:
a communication device configured for:
receiving one or more muscle data from one or more sensors, wherein the one or more sensors is configured for generating the one or more muscle data based on detecting a muscle activation of one or more muscles of one or more first users, wherein the one or more sensors comprises one or more thermal sensors, wherein the one or more thermal sensors is configured for sensing a thermal activity of the one or more muscles of the one or more first users, wherein the detecting of the muscle activation is based on the sensing of the thermal activity;
receiving one or more first biological metrics of the one or more first users from one or more first devices;
receiving one or more second biological metrics of one or more second users from one or more second devices; and
transmitting one or more muscle activation commands to one or more muscle stimulators disposable on the one or more body parts of the one or more second users, wherein the one or more muscle stimulators is configured for stimulating the one or more muscles of the one or more second users based on the one or more muscle activation commands, wherein the stimulating comprises the muscle activation of the one or more muscles of the one or more second users;
a processing device communicatively coupled with the communication device, wherein the processing device is configured for:
analyzing the one or more muscle data;
generating one or more first muscle activity data of the one or more muscles of the one or more first users based on the analyzing of the one or more muscle data, wherein the one or more first muscle activity data comprises one or more first muscle activities of the one or more muscles of the one or more first users;
analyzing the first muscle activity data, the one or more first biological metrics, and the one or more second biological metrics;
transforming the one or more first muscle activities into one or more second muscle activities of the one or more muscles of the one or more second users based on the analyzing of the first muscle activity data, the one or more first biological metrics, and the one or more second biological metrics; and generating the one or more muscle activation commands for the muscle activation of the one or more muscles of the one or more second users based on the one or more second muscle activities; and a storage device communicatively coupled with the processing device, wherein the storage device is configured for storing the first muscle activity data and the one or more muscle activation commands.

11. The system of claim 10, wherein the one or more first user devices comprises one or more first biological sensors, wherein the one or more first biological sensors is configured for generating the one or more first biological metrics based on measuring one or more of a physical parameter and a physiological parameter of a body of the one or more first users.

12. The system of claim 10, wherein the one or more second user devices comprises one or more second biological sensors, wherein the one or more second biological sensors is configured for generating the one or more second biological metrics based on measuring one or more of a physical parameter and a physiological parameter of a body of the one or more second users.

13. The system of claim 10, wherein the one or more sensors comprises one or more electromyography (EMG) sensors, wherein the one or more EMG sensors is disposable on one or more body parts of the one or more first users, wherein the one or more EMG sensors is configured for sensing an electrical activity of the one or more muscles of the one or more first users, wherein the detecting of the muscle activation is based on the sensing of the electrical activity.

14. The system of claim 10, wherein the one or more sensors comprises one or more mechanomyogram (MMG) sensors, wherein the one or more MMG sensors is disposable on one or more body parts of the one or more first users, wherein the one or more MMG sensors is configured for sensing a mechanical activity of the one or more muscles of the one or more first users, wherein the detecting of the muscle activation is based on the sensing of the mechanical activity.

15. The system of claim 10, wherein the detecting of the muscle activation of the one or more muscles of the one or more first users comprises detecting the muscle activation of the one or more muscles of the one or more first users during one or more user activities performed by the one or more first users, wherein the one or more first muscle activity data comprises the one or more first muscle activities corresponding to the one or more user activities performed by the one or more first users, wherein the one or more muscle activation commands corresponds to the one or more user activities.

16. The system of claim 15, wherein the communication device further configured for:

receiving one or more user activity indications associated with one or more first user activities from the one or more second devices; and transmitting one or more first muscle activation commands to the one or more muscle stimulators, wherein the stimulating comprises stimulating the one or more muscles of the one or more second users corresponding to the one or more first user activities, wherein the processing device is further configured for identifying the one or more first user activities based on the one or more user activity indications, wherein the storage device is further configured for retrieving the one or more first muscle activation commands corresponding to the one or more first user activities based on the identifying.

17. The system of claim 10, wherein the communication device further configured for:

transmitting one or more second muscle activity data to the one or more second devices; and receiving one or more adjustments for adjusting the one or more second muscles activities from the one or more second devices, wherein the processing device is further configured for:

generating the one or more second muscle activity data of the one or more muscles of the one or more second users based on the transforming, wherein the one or more second muscle activity data comprises the one or more second muscles activities; and analyzing the one or more adjustments, wherein the generating of the one or more muscle activation commands is further based on the analyzing of the one or more adjustments.

18. The system of claim 10, wherein the one or more first muscles activities comprises a sequence of muscle activation of the one or more muscles of the one or more first users and a strength of muscle activation of the one or more muscles of the one or more first users, wherein the one or more second muscles activities comprises the sequence of muscle activation of the one or more muscles of the one or more second users and the strength of muscle activation of the one or more muscles of the one or more second users.

* * * * *